(12) United States Patent
MacLaughlan

(10) Patent No.: US 11,819,508 B2
(45) Date of Patent: Nov. 21, 2023

(54) MILTEFOSINE FOR THE TREATMENT OF VIRAL INFECTIONS INCLUDING COVID-19

(71) Applicant: Profounda Health and Beauty Inc., Orlando, FL (US)

(72) Inventor: Todd Ewen MacLaughlan, Orlando, FL (US)

(73) Assignee: Profounda Health and Beauty Inc., Orlando, FL (US)

( * ) Notice: Subject to any disclaimer, the term of this patent is extended or adjusted under 35 U.S.C. 154(b) by 0 days.

(21) Appl. No.: 17/471,070

(22) Filed: Sep. 9, 2021

(65) Prior Publication Data

US 2022/0072016 A1 Mar. 10, 2022

Related U.S. Application Data

(60) Provisional application No. 63/075,853, filed on Sep. 9, 2020.

(51) Int. Cl.
| | |
|---|---|
| *A61K 31/661* | (2006.01) |
| *A61K 31/593* | (2006.01) |
| *A61K 38/21* | (2006.01) |
| *A61K 31/573* | (2006.01) |
| *A61K 39/42* | (2006.01) |
| *A61K 9/00* | (2006.01) |
| *A61K 39/00* | (2006.01) |

(52) U.S. Cl.
CPC .......... *A61K 31/661* (2013.01); *A61K 9/0053* (2013.01); *A61K 31/573* (2013.01); *A61K 31/593* (2013.01); *A61K 38/21* (2013.01); *A61K 39/42* (2013.01); *A61K 2039/545* (2013.01)

(58) Field of Classification Search
CPC ................................................... A61K 31/661
See application file for complete search history.

(56) References Cited

U.S. PATENT DOCUMENTS

2020/0215185 A1\* 7/2020 Yuen .................... A61K 31/685

OTHER PUBLICATIONS

Alireza Latifi, Infectious Diseases, 2020, 13: 1178633720977488.\*
Johnson Raymond, BMJ, 2020, 370: m2648.\*
Rios-Marco et al., Alkylphospholipids: An update on molecular mechanisms and clinical relevance, Biochimica et Biophysica Acta (BBA)—Biomembranes, 2017, pp. 1657-1667, vol. 1859—Issue 9—Part B.
Fajnzylber et al., SARS-CoV-2 viral load is associated with increased disease severity and mortality, Oct. 30, 2020, Nature Communications 11, 5493 (2020), 9pgs.

\* cited by examiner

*Primary Examiner* — Rei Tsang Shiao
(74) *Attorney, Agent, or Firm* — Dentons Cohen & Grigsby P.C.

(57) ABSTRACT

Methods of treating infections caused by viruses such as influenza and coronaviruses are disclosed. The methods generally include systemic administration of an effective amount of miltefosine, such as an oral or intravenous formulation, and optionally administration of one or more secondary agents. The methods may alleviate or abrogate the viral infection and may further lessen the effects of the cytokine and/or bradykinin storms that occur in certain subjects.

19 Claims, No Drawings

MILTEFOSINE FOR THE TREATMENT OF VIRAL INFECTIONS INCLUDING COVID-19

CROSS REFERENCE TO RELATED APPLICATIONS

The present application claims the benefit under 35 U.S.C. § 119(e) of prior U.S. Provisional Application Ser. No. 63/075,853, filed Sep. 9, 2020, the content of which is incorporated by reference here into this application.

FIELD OF THE INVENTION

The present invention relates to methods for treating a subject having a viral infection using systemic and/or local administration of miltefosine alone or in combination with one or more secondary agents.

BACKGROUND OF THE INVENTION

Viruses do not possess genes that encode for the proteins required for translation, energy metabolism, or membrane biosynthesis, and therefore depend on a host cell to replicate. The virus uses a diverse spectrum of virally encoded proteins that affect a broad spectrum of host cellular pathways to ensure their successful propagation. For example, the PI3K/Akt/mTOR signaling pathway of the host cell plays a critical regulatory role in many cellular processes including RNA processing, translation, glucose metabolism, protein synthesis, autophagy, and apoptosis, and as such is the target for many viruses. Basal activity of this pathway ensures cell survival, while inactivation of PI3K/Akt/mTOR signaling results in apoptosis. For an infected organism, apoptosis represents an effective antiviral instrument that is simple but highly effective. Thus, in order to secure its own replication, the virus must prevent or delay apoptosis. Agents that may inhibit PI3K/Akt/mTOR signaling may provide an effective treatment for viral infections.

Viral infections have also been found to be causative for cytokine storms during the later stages of the disease and/or recovery. Cytokine storm is a general term applied to maladaptive cytokine release in response to infection and other stimuli. The pathogenesis is complex but includes loss of regulatory control of proinflammatory cytokine production, both at local and systemic levels. The disease progresses rapidly, causing tissue damage and even eventual mortality.

The severe acute respiratory syndrome coronavirus (SARS-CoV), while generally known to cause respiratory infections, has recently been noted to be the causative agent in a wide range of disorders, including intestinal, cardiac, and vascular dysfunction. Recent evidence from studies with the SARS-CoV-2 (Covid-19) indicate that these responses to a SARS-CoV infection may stem from the virus's upregulation of angiotensin converting enzyme (ACE) receptors and interaction with the renin-angiotensin system (RAS), which controls the body's level of bradykinin. Excessive bradykinin, i.e., a bradykinin storm, has been found to lead to vascular permeability, causing the lungs to fill with fluids that include leaked immune cells, and a breakdown of the blood-brain barrier, leading to inflammation and potential brain damage. In addition to inflammation of the lungs and brain, bradykinin storms may also be causative of certain cardiac symptoms, such as arrhythmias and low blood pressure.

Accordingly, an object of the presently disclosed invention is to provide agents and methods of their use that may counteract or slow down the rate of viral activation of the PI3K/Akt/mTOR signaling pathway. Another object of the presently disclosed invention is to provide one or more additional agents that may address the immune dysregulation, and thus the severity of the inflammation that is part of the cytokine and bradykinin storms that occur in certain subjects upon viral infection.

SUMMARY OF THE INVENTION

The presently disclosed invention is based on the discovery that administration of miltefosine (2-[[(hexadecyloxy) hydroxyphosphenyl]oxy]-N,N,Ntrimethylethylammonium inner salt, also known as hexadecylphosphocholine) alone or in combination with one or more secondary agents provides an effective treatment for viral infections.

Accordingly, disclosed are compositions and treatment methods for infections caused by a virus. The methods generally comprise administration of an effective amount of miltefosine. The miltefosine may be provided systemically, such as intravenously or by an oral formulation (e.g., pill, capsule, liquid) that may be ingested by a subject or administered to a subject undergoing treatment, and optionally may also be provided locally, such as an aerosolizable formulation (e.g., for administration via an inhaler or nebulizer).

Administration of the miltefosine may be continued on a daily basis (from 1-8 times per day) for a period of time of at least one day to at least 10 days, such as up to one or more months.

The methods may be used to treat subjects with viral infections caused by an influenza virus or a coronavirus.

The viral infection(s) treated by the methods of the presently disclosed invention may be those caused by a severe acute respiratory syndrome coronavirus (SARS-CoV), such as SARS-CoV-2 or Covid-19.

The disclosed methods may further comprise administration of one or more secondary agent(s), such as one or more PI3K/AKT/mTOR inhibitors, antiviral agents, immunomodulatory agents, steroidal agents, antipyretic agent, and anti-anaphylaxis agents. The secondary agent may be provided as an intravenous formulation, intramuscular injection, oral formulation (e.g., liquid, liquigel, capsule, tablet), or a topical or local formulation (e.g., cream, ointment, inhaled formulation).

The secondary agent may be an immunomodulatory agent, such as an interferon and/or vitamin D. According to certain aspects, the secondary agent may be a steroidal agent such as a corticosteroid. According to certain aspects, the secondary agent may be an antiviral agent, such as a monoclonal antibody against a spike protein of the infecting virus (e.g., casirivimab and imdevimab, which are directed against the spike protein RBD of SARS-CoV-2).

The systemically provided miltefosine may be administered at a first dose for a first time period, and at a second dose for a second time period. The second dose may be lower than the first dose. The time period of the second dose, however, may be longer than the time period of the first dose.

For example, the first dose may include a dose of 10 milligrams/day (i.e., 10 mg/day) to 200 mg/day, and the second dose may include a dose of 5 mg/day to 150 mg/day. Alternatively, the first dose may include a dose of 1 mg/kg/day to 10 mg/kg/day, and the second dose may include a dose of 0.5 mg/kg/day to 5 mg/kg/day. The first time period may be from at least 1 day to at least one week, and the second time period may be from at least 3 days to at least three months, wherein the second time period is subsequent to the first time period. The first and second doses may be administered one, two, three or more times per day as portions of the daily dose. For example, the portions of the daily dose may be equal portions.

The systemically provided miltefosine may be administered, such as at the first dose, starting after symptoms of the viral infection are evident. For example, the systemically provided miltefosine may be administered after a subject's oxygen saturation level drops below normal, such as below 96%, or below 94%, or below 92%, or below 90%, or below 88%, or even below 86%. According to certain aspects, the systemically provided miltefosine may be administered after the subject's oxygen saturation level drops below normal, but before the subject is placed in oxygen therapy.

The locally provided miltefosine may be administered hourly or daily during the first time period, and less frequently in the second time period (e.g., first and second time periods of the systemically provided miltefosine). According to certain aspects of the presently disclosed invention, the locally provided miltefosine may be a formulation comprising 5 µM to 2500 µM miltefosine or may be a formulation configured to provide 0.05 µM to 500 µM miltefosine in the blood or 0.1 µM to 50 µM miltefosine in the cerebral spinal fluid (CSF) or tears of a subject being treated. Exemplary local formulations include inhaled and aerosolized formulations.

The objects of the present invention will be realized and attained by means of the combinations specifically outlined in the appended claims. The foregoing general description and the following detailed description and examples of this invention are provided to illustrate various aspects of the present invention, and by no means are to be viewed as limiting any of the described embodiments.

Definitions and Abbreviations

Throughout this description and in the appended claims, use of the singular includes the plural and plural encompasses singular, unless specifically stated otherwise. For example, although reference is made herein to "an" infection, "a" composition, or "the" pharmaceutical carrier, one or more of any of these components and/or any other components described herein may be used.

The word "comprising" and forms of the word "comprising", as used in this description and in the claims, does not limit the present invention to exclude any variants or additions. Additionally, although the present invention has been described in terms of "comprising", the processes, materials, and compositions detailed herein may also be described as consisting essentially of or consisting of. For example, while certain aspects of the invention have been described in terms of a method comprising administering a therapeutically effective amount of miltefosine with or without a corticosteroid, a method "consisting essentially of" or "consisting of" administering the miltefosine with or without the corticosteroid is also within the present scope. In this context, "consisting essentially of" means that any additional components will not materially affect the efficacy of the method.

Moreover, other than in the examples, or where otherwise indicated, all numbers expressing, for example, quantities of ingredients used in the specification are to be understood as being modified in all instances by the term "about". Accordingly, unless indicated to the contrary, the numerical parameters set forth in the following specification are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements. When ranges are given, any endpoints of those ranges and/or numbers within those ranges can be combined within the scope of the present invention.

"Virus" as used herein may refer to any of influenza, coronavirus, norovirus, parvovirus, sindbis virus, dengue virus, adenovirus, Epstein-Barr virus (EBV), respiratory syncytial virus (RSV), vaccinia virus, rhinovirus, human immunodeficiency virus (HIV), cytomegalovirus (CMV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, viral pneumonia, papillomavirus, west Nile virus, yellow fever virus and others.

Coronaviruses (CoVs) are the largest known single-stranded, positive-strand RNA viruses. The International Committee on Taxonomy of Viruses (ICTV) classifies the CoVs into four categories: α, β, γ, and δ. Under the electron microscope, the virus particles display a rough spherical or multi-faceted crystal shape having prominent club-shaped projections composed of its spike protein on the surface. CoVs can infect a variety of host species, including birds, humans and some other vertebrates. These viruses mainly cause respiratory and intestinal infections and induce a variety of clinical manifestations.

So far, seven CoVs capable of invading humans have been identified, including the α-type HCoV-229E and HCoV-NL63; the β-type HCoV-HKU1, SARS-CoV, MERS-CoV, and HCoV-OC43; and 2019-nCoV, causing the present epidemic. According to their pathogenicity, HCoVs are divided into mildly pathogenic HCoVs (including HCoV-229E, HCoV-OC43, HCoV-NL63, and HCoV-HKU) and highly pathogenic CoVs (including severe acute respiratory syndrome CoV (SARS-CoV)), Middle East respiratory syndrome coronavirus (MERS-CoV) and SARS-CoV-2, i.e., Covid-19. The mildly pathogenic HCoVs infect the upper respiratory tract and cause seasonal, mild to moderate cold-like respiratory diseases in healthy individuals. In contrast, the highly pathogenic HCoVs (hereinafter referred to as pathogenic HCoVs or HCoVs) infect the lower respiratory tract and cause severe pneumonia, sometimes leading to fatal acute lung injury (ALI) and acute respiratory distress syndrome (ARDS).

"Synergistic combinations," as used herein, are combinations of monotherapies that may provide a therapeutic effect that is comparable to the effectiveness of a monotherapy, while reducing adverse side effects of the monotherapy, e.g. effects of a cytokine storm potentially caused by the viral infection and/or the PI3K/AKT/mTOR inhibitor. Alternatively, synergistic combinations may provide for an improved therapeutic effectiveness, which may be measured by a reduction in the total viral load or a length of time of the viral infection, or an improvement in other indicators of subject health. Synergistic combinations of the present invention may combine a therapeutically effective amount of miltefosine with a therapeutically effective amount of one or more secondary agents.

As used herein, "Cytokine storm" may be understood to mean the uncontrolled and excessive release of cytokines from an activated immune system. Cytokines are small proteins released by many different cells in the body, including those of the immune system where they coordinate the body's response against infection and trigger inflammation. For example, when a virus enters the lungs, it triggers an immune response, attracting immune cells to the region to attack the virus, resulting in localized inflammation. In certain subjects, excessive or uncontrolled levels of cytokines are released which then activate more immune cells, resulting in hyperinflammation, a condition that may cause serious damage to the affected tissues and may even kill the subject. Cytokine storms are a common complication of SARS-CoV-2 and influenza, and certain other respiratory diseases caused by coronaviruses such as SARS and MERS. Cytokine release syndrome (CRS) is a condition in which the rapid and massive release of cytokines into the bloodstream leads to dangerously low blood pressure, high fever and shivering.

As used herein, "Bradykinin storm" may be understood to mean the uncontrolled and excessive buildup of bradykinins, such as through dysregulation of the RAS (e.g., inhibition of bradykinin's degradation by inhibition of ACE). Bradykinin is a peptide that promotes the release of prostacyclin, nitric oxide, and endothelium-derived hyperpolarizing factor in arterioles causing them to dilate, and the release of prostaglandin F2 in veins causing them to constrict. This combined action leads to leakage into capillary beds due to the increased pressure in the capillaries. Bradykinin is a physiologically and pharmacologically active peptide of the kinin group of proteins, consisting of nine amino acids.

"Pharmaceutically acceptable salt" refers to acid addition salts of basic compounds, e.g., those compounds including a basic amino group, and to basic salts of acidic compounds, e.g., those compounds including a carboxyl group, and to amphoteric salts of compounds that include both an acidic and a basic moiety, such that these salts are suitable for administration in vivo, preferably to humans. Various organic and inorganic acids may be used for forming acid addition salts. Pharmaceutically acceptable salts are derived from a variety of organic and inorganic counter ions well known in the art. Pharmaceutically acceptable salts include, when the molecule contains a basic functionality, by way of example only, hydrochloride, hydrobromide, tartrate, mesylate, acetate, maleate, oxalate and the like, and when the molecule contains an acidic functionality, by way of example only, sodium, potassium, calcium, magnesium, ammonium, tetraalkylammonium, N-methylmorpholinium, and the like. In one embodiment, the pharmaceutically acceptable salt of ezatiostat is ezatiostat hydrochloride.

"Treat" or "treatment" refers to therapeutic treatment wherein the object is to slow down (lessen) an undesired physiological change or disease, such as the development or spread of an infection, or to provide a beneficial or desired clinical outcome during treatment. Beneficial or desired clinical outcomes include alleviation of symptoms, diminishment of extent of infection, stabilization (i.e., not worsening) of the state of infection, delay or slowing of infection progression, and amelioration or palliation of the infection state or the negative effects of such infection that may occur immediately or over time. "Treatment" may also mean prolonging survival as compared to expected survival if a subject was not receiving treatment. Those in need of treatment include those subjects already presenting with the undesired physiological change or disease as well as those subjects prone to have the physiological change or disease.

The phrase "therapeutically effective amount" as used herein refers to an amount sufficient to provide treatment as defined herein and may include an amount effective to inhibit viral expansion. That is, reference to administration of the therapeutically effective amount of miltefosine according to the methods or compositions of the disclosed invention may be taken to refer to a therapeutic effect in which substantial antiviral activity causes a substantial inhibition of the viral infection. As such, a therapeutically effective amount may refer to a sufficient amount of the composition to provide the desired biological, therapeutic, and/or prophylactic result. The desired results include elimination of viral infection or colonization or reduction and/or alleviation of the signs, symptoms, or causes of a viral infection, or any other desired alteration of a biological system, such as indicated above with regard to synergistic combinations. In relation to a pharmaceutical or veterinary composition, effective amounts can be dosages that are recommended in the modulation of a diseased state or signs or symptoms thereof. Effective amounts may differ depending on the composition used and the route of administration employed. Effective amounts are routinely optimized taking into consideration various factors of a particular subject, such as age, weight, gender, etc. and the severity of the biological response to the infection.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. "Subject" and "subject" are used interchangeably herein.

Unless otherwise defined, all technical and scientific terms used herein have the same meaning as commonly understood by one of ordinary skill in the art to which the present invention belongs. Although methods and materials similar or equivalent to those described herein can be used in the practice or testing described herein, suitable methods and materials are described below.

DETAILED DESCRIPTION OF THE INVENTION

The presently disclosed invention provides compositions and methods useful for treating a viral infection, such as an infection caused by an influenza virus or a coronavirus. The compositions and methods may reduce the viral load of an infected subject through interventions in the early stages of the infection, and optionally by controlling inflammatory responses prevalent during later stages of the infection. According to certain aspects, miltefosine may be administered for at least one week to reduce proliferation of the virus. According to certain other aspects, one or more secondary agents, such as an immunomodulator or steroid, may be administered to address the cytokine storm that occurs in certain subjects during later stages of the infection.

Viral Infections

The presently disclosed compositions and methods may be used to treat a subject with a viral infection. Exemplary viral infections may be caused by a wide range of viruses, such as influenza, coronavirus, norovirus, parvovirus, sindbis virus, dengue virus, adenovirus, Epstein-Barr virus (EBV), respiratory syncytial virus (RSV), vaccinia virus, rhinovirus, human immunodeficiency virus (HIV), cytomegalovirus (CMV), human papillomavirus (HPV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, viral pneumonia, papillomavirus, west Nile virus, yellow fever virus and others.

Of particular interest are the influenza and coronaviruses. Exemplary coronaviruses include at least coronaviruses (CoVs) that can invade humans, including those responsible for severe acute respiratory syndrome (SARS), such as SARS-CoV. An exemplary virus of particular interest is the SARS-CoV-2 or Covid-19 causing the present epidemic. These highly pathogenic HCoVs infect the lower respiratory tract and cause severe pneumonia, sometimes leading to fatal acute lung injury (ALI) and acute respiratory distress syndrome (ARDS). The Covid-19 virus has also been found to be causative of a wide range of additional, non-respiratory symptoms, such as cardiac and vascular dysfunction and disease, brain inflammation, loss of taste and smell, loss of speech and movement, skin rashes, discoloration of the fingers and toes ("covid-toes"), and digestive and intestinal issues. Many of these symptoms may stem from the secondary effects the virus has on the RAS and immune system. For example, many of these symptoms are similar to those observed with cytokine and bradykinin storms.

Accordingly, the presently disclosed invention provides compositions and methods for the treatment viral infections, such as those cause by influenza or coronaviruses. Such infections have typically been hard to treat as the virus does not comprise systems of its own that may be targeted. Rather, the virus co-opts the cellular systems of the host. Moreover, the presentation of infection symptoms and severity vary greatly with each subject based on a range of factors, including at least age and/or other pre-existing conditions. Accordingly, methods that may be successful on one subject group may not work on another. The methods disclosed herein may overcome certain of these prior limitations by providing miltefosine alone or in combination with one or more secondary agents to address several issues observed in viral infections.

Systemic Miltefosine

The chemical name of miltefosine is 2-[[(hexadecyloxy) hydroxyphosphenyl]oxy]-N,N,N-trimethylethylammonium inner salt, also known as hexadecylphosphocholine, represented by the formula (I). The empirical formula is $C_{21}H_{46}NO_4P$, yielding a molecular weight of 407.57 g/mol. Miltefosine is a white powder that is freely soluble in water, 0.1 N HCl or NaOH, methanol, and ethanol.

mTOR) intracellular signaling pathway, which is involved in cell survival. (Rios-Marco, P, et al. *Alkylphospholipids: An update on molecular mechanisms and clinical relevance*, Biochemica et Biopysica Acta (2017) vol. 1859, pg. 1657-67).

Since miltefosine has been found to have a long half-life and is known to cross the blood-brain barrier, the present inventor believed that either systemically, or systemically and locally (e.g., locally, such as to the lungs via an inhaler or nebulizer, or as an intravenous bolus to a specific location within the body), the drug would be useful to inhibit viral infection and expansion.

Thus, the presently disclosed invention includes methods for treatment of viral infections by providing miltefosine systemically, such as by administering miltefosine intravenously or as an oral formulation, for at least 1 day, such as 2, 3, 4, 5, 6, 7, 8, 9, or 10 days. The miltefosine may be provided for at least one week, such as 2, 3, or even 4 weeks. For example, the methods may include systemic administration of the miltefosine at a total daily dose of 10 milligrams/day (i.e., 10 mg/day) to 200 mg/day, such as 20 mg/day to 150 mg/day, or 50 mg/day to 150 mg/day. Administration may be in one or more doses spread throughout the day, such as one, two, three, or more doses, so that a total of all doses administered in one day provide the total daily dose (e.g., administering one, two, or three 50 mg tablets per day will provide a total daily dose of 50 mg, 100 mg, or 150 mg, respectively).

The methods may include systemic administration of miltefosine at a total daily dose of at least 10 mg/day, such as at least 20 mg/day, or at least 30 mg/day, or at least 40 mg/day, or at least 50 mg/day, or at least 60 mg/day, or at least 70 mg/day, or at least 80 mg/day, or at least 90 mg/day, or at least 100 mg/day, or at least 110 mg/day, or at least 120 mg/day, or at least 130 mg/day, or at least 140 mg/day, or at least 150 mg/day. The methods may include systemic administration of miltefosine at a total daily dose of up to 300 mg/day, such as up to 280 mg/day, or up to 260 mg/day, or up to 250 mg/day, or up to 240 mg/day, or up to 220 mg/day, or up to 200 mg/day, or up to 190 mg/day, or up to 180 mg/day, or up to 170 mg/day, or up to 160 mg/day, or up to 150 mg/day. Dosage ranges defined by any combination of lower and upper doses are possible and within the scope of the present invention.

The methods may also include systemic administration of miltefosine at a total daily dose calculated based on subject weight, such as at a total daily dose of 0.5 mg/kg/day to 10

Formula I

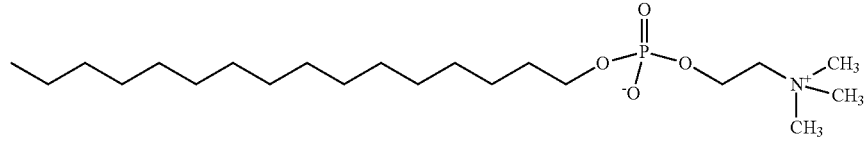

Miltefosine belongs to the class of alkylphosphocholine drugs, which are phosphocholine esters of aliphatic long-chain alcohols. These alkylphosphocholine compounds are structurally related to the group of alkyl-lysophospholipids, which are synthetic analogues of lysophosphatidylcholines or lysolecithins, but lack their glycerol backbone. From a functional point of view, miltefosine is considered an inhibitor of Akt, otherwise known as protein kinase B (PKB). Akt/PKB is a crucial protein within the phosphatidylinositol 3-kinase/Akt/mammalian target of rapamycin (PI3K/Akt/ mg/kg/day, or 1 mg/kg/day to 8 mg/kg/day, or 1 mg/kg/day to 6 mg/kg/day, wherein the total daily dose may be administered in one, two, three or more doses throughout the day. As example, for oral administration to a 50 kg subject, the miltefosine may be administered as one, two, or three 50 mg tablets or capsules per day to provide a total daily dose of 1 mg/kg/day, 2 mg/kg/day, or 3 mg/kg/day, respectively. Accordingly, the methods may include systemic administration of miltefosine at a total daily dose of at least 0.5 mg/kg/day, such as at least 0.5 mg/kg/day, or at least 1.0 mg/kg/day, or at least 1.5 mg/kg/day, or at least 2.0 mg/kg/day, or at least 2.5 mg/kg/day, or at least 3.0 mg/kg/day. The methods may also include systemic administration of miltefosine at a total daily dose of up to 10 mg/kg/day, such as up to 8 mg/kg/day, or up to 6 mg/kg/day, or up to 4 mg/kg/day. Dosage ranges defined by any combination of lower and upper doses are possible and within the scope of the present invention.

In other examples, the miltefosine may be administered via intravenous infusion, wherein the dose may be administered continuously throughout the day to provide the total daily dose or may be administered as boluses comprising a portion of the total daily dose infused over a shorter period of time, such as three doses infused over a one-hour period wherein each dose comprises $\frac{1}{3}$ of the total daily dose.

While specific examples have been provided for illustrative purposes, various other portions and timings of intravenous boluses or oral doses are envisioned and within the scope of the present invention.

The methods of the presently disclosed invention may include systemic administration of the miltefosine according to more than one dosage regime, wherein each dosage regime includes the miltefosine administered at a total daily dose in one, two, three, or more doses or portions for a specific period of time. For example, the methods may include administration of the miltefosine according to a first dosage regime primarily focused on rapid reduction of the viral load, followed by administration of the miltefosine according to a second dosage regime primarily focused on full eradication of the viral infection. The methods may include systemic administration of miltefosine according to a first dosage regime or "loading dose" comprising a first dose for a first time period of at least one day to several days, or even a week to 10 days, followed by systemic administration of miltefosine at a second dosage regime or "sustained dose" for a second time period of at least several days to several weeks or months, wherein the second dosage regime is subsequent to the first dosage regime.

According to certain aspects of the presently disclosed invention, the first dosage regime may comprise the miltefosine administered systemically at a total daily dose as defined hereinabove, such as of 10 mg/day to 200 mg/day, or 20 mg/day to 150 mg/day, or 50 mg/day to 150 mg/day, in one, two, three, or more doses. For example, the miltefosine may be administered in 50 mg doses two or three times per day (i.e., providing the total daily dose of 100 mg/day or 150 mg/day, respectively) for a period of one day to several days or even one week.

After the miltefosine is administered according to the first dosage regime, it may be administered according to a second dosage regime, wherein the second dosage regime may comprise administering the miltefosine at a total daily dose of 5 mg/day to 150 mg/day for a time period of at least several days to several weeks, such as at least one to two weeks.

According to certain aspects of the presently disclosed invention, the second dosage regime may comprise administering the miltefosine at a total daily dose of 10 mg/day to 150 mg/day, such as 10 mg/day, or 20 mg/day, or 30 mg/day, or 40 mg/day, or 50 mg/day, or 60 mg/day, or 70 mg/day, or 80 mg/day, or 90 mg/day, or 100 mg/day, or 110 mg/day, or 120 mg/day, or 130 mg/day, or 140 mg/day, or 150 mg/day in one, two, three, or more doses per day. For example, the miltefosine may be administered in 10 mg doses two or three times per day (i.e., providing the total daily dose of 20 mg/day or 30 mg/day, respectively). Alternatively, the miltefosine may be administered in 50 mg doses two or three times per day (i.e., providing the total daily dose of 100 mg/day or 150 mg/day, respectively).

Alternatively, the first dose may include a dose of 1 mg/kg/day to 10 mg/kg/day, and the second dose may include a dose of 0.5 mg/kg/day to 5 mg/kg/day. The first and second doses may be as defined hereinabove, such as comprising at least a lower dose and up to an upper dose, wherein any combination of lower and upper doses may define a dosage range. In general, however, the total daily dose in the second dosage regime is lower than the total dose in the first dosage regime.

Day one of administration of the systemic miltefosine may be based on onset of certain symptoms of the viral infection. For example, the systemically provided miltefosine may be administered upon positive diagnosis of a viral infection (PCR, rapid antigen, etc.), but after a subject's oxygen saturation level drops below normal, wherein a normal oxygen saturation level is at least 97%. Accordingly, commencement of administration of the systemically provided miltefosine may be after a subject's oxygen saturation level drops below 96%, such as below 94%, or below 92%, or below 90%, or below 88%, or even below 86%.

According to certain aspects, day one of the administration of systemically provided miltefosine may be upon positive diagnosis of a viral infection and after the subject's oxygen saturation level drops below normal, but before the subject is placed on oxygen therapy.

Standard oxygen therapy starts with providing oxygen via a nasal cannula at 6 liters per minute covered with a surgical mask (level a). The oxygen therapy may be escalated to a Venturi mask, which allows for more precise oxygen titration, such as up to 50% covered with a surgical mask, or non-rebreather if a Venturi mask is not available (level b). Further escalation of the oxygen therapy may include a nasal cannula at 6 liters per minute plus non-rebreather mask up to 15 liters per minute covered with a surgical mask (level c); a high-flow nasal cannula covered with a surgical mask (level d; i.e., delivery of heated, e.g., 37° C., and humidified, e.g., 100% relative humidity, oxygen at concentrations ranging from 21%-100% at flow rates reaching 60 liters per minute); a continuous positive airway pressure (CPAP) device with a viral filter (level e); and finally the most aggressive therapy may include endotracheal intubation (level f).

Accordingly, day one of the administration of systemically provided miltefosine may be upon positive diagnosis of a viral infection and after the subject's oxygen saturation level drops below normal, but before the subject is placed on any step of the oxygen therapy listed in the above indicated progression (i.e., before the subject is placed on level a, b, c, d, e, or f of the oxygen therapy).

According to certain aspects, commencement of administration of the systemically provided miltefosine may be upon positive diagnosis of a viral infection (PCR, rapid antigen, etc.) for high-risk subjects. High-risk subjects may be defined by any of a number of factors, such as a subject presenting with a high viral load (VL) or a rapidly increasing VL, a subject who is older (i.e., above the age of 65), a subject who is pregnant or recently pregnant, or a subject presenting with another disease or disorder associated with poor outcome for the viral infection.

The seriousness of symptoms from viral infections is often due directly to the amount of the virus that gets into the subject's body. In addition, studies on two previous coronaviruses (SARS and MERS) showed that subjects exposed to higher VL got sicker. The VL is commonly expressed in units of $\log_{10}$ RNA copies/ml. A high VL, as used herein, should be understood to mean any VL that is greater than the standard, mean, or median VL of a subject population presenting with the same viral infection. For SARS-CoV-2, one study found that a standard VL in a subject is generally about 2 $\log_{10}$ RNA copies/ml detected in plasma and 4 $\log_{10}$ RNA copies/ml detected in sputum. Thus, for a subject with a SARS-CoV-2 infection, a high VL may be any load greater than 2 $\log_{10}$ RNA copies/ml detected in plasma and greater than 4 $\log_{10}$ RNA copies/ml detected in sputum. The VL was determined using the US CDC 2019-nCoV_N1 primers and probe set by methods detailed in the *SARS-CoV-2 viral load is associated with increased disease severity and mortality* to J. Fajnzylber et al., Nature Communications 11, Article number: 5493 (2020).

VL may also be expressed by Ct values. In quantitative (q) PCR, a positive reaction is detected as the accumulation of fluorescent signal. Cycle threshold (Ct) is defined as the number of cycles required for the fluorescent signal to cross the threshold, i.e. to exceed the background level. Current qRT-PCR protocols for SARS-CoV-2 detection suggest that samples with Ct values less than 40 can be interpreted as positive for viral RNA. According to this standard, a high viral load may be understood to be a Ct value of less than 40, such as less than 35, or even less than 30.

Diseases or disorders associated with poor outcomes for the viral infection include cancer; chronic kidney disease; overweight or obesity; chronic lung disease including COPD (chronic obstructive pulmonary disease), asthma (moderate-to-severe), interstitial lung disease, cystic fibrosis, and pulmonary hypertension; dementia or other neurological conditions; diabetes (types I and II); down syndrome; heart conditions such as heart failure, coronary artery disease, cardiomyopathies or hypertension; HIV infection; immunocompromised or weakened immune systems; liver disease; sickle cell disease or thalassemia; smokers; solid organ or stem cell transplant; stroke or cerebrovascular disease, which affects blood flow to the brain; and substance use disorders.

Local Miltefosine

According to certain aspects of the presently disclosed invention, the miltefosine may also be administered locally, such as via inhaled administration. For example, according to certain aspects, the methods of the presently disclosed invention may include administration of miltefosine both systemically as detailed above and locally.

Local administration of miltefosine may be via injection, such as to a specific location within the body, and/or by inhalation, such as by an inhaler or nebulizer for local delivery to the lungs and airways.

Local administration may occur concurrently with the systemic administration of miltefosine for all or a portion of the administration period of the latter. For example, the locally administered formulation comprising miltefosine may be administered concurrently with the systemic formulation of miltefosine during the first dosage regime, or a portion of the first dosage regime, of the latter. The locally administered formulation comprising miltefosine may be administered concurrently with the systemic formulation of miltefosine during the second dosage regime, or a portion of the second dosage regime, of the latter. The locally administered formulation comprising miltefosine may be administered concurrently with the systemic formulation of miltefosine during the first and second dosage regime of the latter. The locally administered formulation comprising miltefosine may be administered concurrently with the systemic formulation of miltefosine during the first dosage regime and only a portion of the second dosage regime of the latter.

The locally administered formulation comprising miltefosine may be administered before the systemic miltefosine is administered, such as at days −5, −4, −3, −2, −1, or 0.

The locally administered formulation comprising miltefosine may be administered for a time period of at least one day to several weeks.

The local administration of miltefosine may be on a time schedule that is the same as the systemic administration of miltefosine or may be on a different time schedule. For example, the local administration of miltefosine may be hourly, or every two hours, or every three hours during all or a portion of a day.

Miltefosine may be included in the local formulation at from 5 μM to 2500 μM, such as from 10 μM to 1000 μM, or from 10 μM to 500 μM, or even from 20 μM to 200 μM. The miltefosine may be included in a local formulation configured to provide 0.05 μM to 500 μM miltefosine in the blood or 0.1 μM to 50 μM miltefosine in the cerebral spinal fluid (CSF) or tears of a subject being treated.

Miltefosine Formulations

The miltefosine may be provided as a pharmaceutical composition, wherein the composition may be formulated by techniques known to the person skilled in the art, such as the techniques published in Remington's Pharmaceutical Sciences, $20^{th}$ Edition. The pharmaceutical compositions can be formulated as dosage forms for oral, parenteral, such as intramuscular, intravenous, subcutaneous, intradermal, intraarterial, nasal, or topical administration.

Oral formulations may include solid or liquid dosage forms that may be swallowed. Solid and liquid dosage forms for oral administration include coated and uncoated tablets, soft gelatin capsules (e.g., liquigels), hard gelatin capsules, lozenges, troches, solutions, emulsions, suspensions, syrups, elixirs, powders and granules for reconstitution, dispersible powders and granules, medicated gums, chewing tablets and effervescent tablets.

Dosage forms for parenteral administration include solutions, emulsions, suspensions, dispersions and powders and granules for reconstitution. Emulsions are a preferred dosage form for parenteral administration.

Dosage forms for nasal administration can be administered via inhalation and insufflation, for example by a metered inhaler or nebulizer. Since the miltefosine is readily soluble in water or saline solutions, formulations for use in a nebulizer may include an aqueous formulation of miltefosine that may be aerosolized for inhalation via a nebulizer.

Dosage forms for topical administration include creams, gels, ointments, salves, patches and transdermal delivery systems.

According to certain aspects, local administration of miltefosine may be via nasal or oral administration to the lungs, such as by an inhaler or nebulizer, or topical administration, such as via a patch for transdermal delivery.

The miltefosine may be provided as a pharmaceutical composition, wherein the composition may be in the form of a single release formulation, a micronized formulation, or a controlled-release formulation that may include a degradable or non-degradable polymer, hydrogel, organogel, or other physical construct that modifies the release of the compound. It is understood that such formulations may include additional inactive ingredients that are added to provide desirable color, stability, buffering capacity, dispersion, or other known desirable features. Such formulations may further include liposomes, such as emulsions, foams, micelles, insoluble monolayers, liquid crystals, phospholipid dispersions, lamellar layers and the like. Liposomes for use in the invention may be formed from standard vesicleforming lipids, generally including neutral and negatively charged phospholipids and a sterol, such as cholesterol.

According to certain aspects of the presently disclosed invention, the miltefosine is administered as an oral formulation that is a solid, such as a pill, capsule, or the like. As such, the formulations of the miltefosine of the invention may include inactive ingredients, such as colloidal silicon dioxide, microcrystalline cellulose, lactose monohydrate, talc, and magnesium stearate. For example, when formulated as a capsule, the shell may contain gelatin, titanium dioxide, ferric oxide, and purified water.

Miltefosine is freely soluble in aqueous solutions. Thus, according to certain aspects of the presently disclosed invention, the miltefosine may be administered as an oral formulation that is a liquid, such as included in a liquid capsule that may be swallowed, or as a formulation that a subject may drink. The miltefosine may be applied directly to body tissues such as skin or cornea. Alternatively, the miltefosine may be formulated as a solution that may be administered intravenously, such as formulated in a sterile saline solution.

According to certain aspects of the presently disclosed invention, the miltefosine may be administered locally and may comprise a topical composition formulated to include buffer components and salts (phosphate salts or other buffering salts, such as TRIS) in an amount effective in maintaining the pH of the solution within a physiologically acceptable range, preferably with a pH between 6 and 8. The topical composition may be formulation to include a preservative. For example, when the topical formulation is an ophthalmic composition, a preservative may be included. The term "preservative" or like terms denotes agents included in the compositions for the purpose of inhibiting the growth of microorganisms in the product, thereby helping to maintain sterility of the composition. Topical formulations may also include antimicrobial agents. The term "antimicrobial agent" denotes a specific active agent which provides antimicrobial efficacy.

Secondary Agents

According to certain aspects, the methods of the presently disclosed invention further comprise administering to the subject one or more additional therapeutic agents for the disease, disorder, or condition. The additional therapeutic or secondary agent may be administered concurrently with the systemic administration of miltefosine for all or a portion of the administration period of the miltefosine. For example, the secondary agent may be administered concurrently with the systemic administration of miltefosine during a first dosage regime, or a portion of the first dosage regime, of the miltefosine. The secondary agent may be administered concurrently with the systemic administration of miltefosine during a first and second dosage regime of the miltefosine. The secondary agent may be administered concurrently with the systemic administration of miltefosine during the first dosage regime and only a portion of the second dosage regime of the miltefosine. The secondary agent may be administered before the systemic and/or local administration of miltefosine is initiated (e.g., at days −10, −9, −8, −7, −6, −5, −4, −3, −2, −1, 0 of the administration of the systemic and/or local miltefosine).

The secondary agent may be administered intravenously, topically, or orally as a liquid composition. The secondary agent may be administered topically or orally as a solid composition (e.g., cream/ointment or pill) or as a solid tablet, capsule, or the like to be ingested by the subject.

Exemplary secondary agents include at least PI3K/AKT/mTOR inhibitors, antiviral agents, immunomodulatory agents, steroidal agents, antipyretic agents, and anti-anaphylaxis agents.

(a) PI3K/Akt/mTOR Inhibitors

One or more additional PI3K/Akt/mTOR inhibitors may help to reduce the viral load, especially if administered during the early stages of the infections and/or the early stages of the presently disclosed methods (e.g., the first treatment period). Exemplary PI3K/mTOR pathway inhibitors include at least GDC-0941, NVP-BKM120, PKI-402, BX-912, BNP-BEZ235, wortmannin, rapamycin and related binding partner tacrolimus, everolimus, and imidazole-oxindole C16. Preferred inhibitors include BX-912, BNP-BEZ235, wortmannin, everolimus, tacrolimus, and rapamycin, dosage regimes for which are known in the art.

(b) Antiviral Agents

According to certain aspects, the secondary agent is an antiviral agent. Examples of antiviral agents include, without limitation, rimantadine, amantadine, oseltamivir (TAMIFLU®), laninamivir (INAVIR®), zanamivir (RELENZA®), peramivir (RAPIVAB®), tamiphosphor, favipiravir, VX-787, AL794, S-033188, AB103, TCAD Combo, Avi-7100, flufivirtide-3, fluconazole (FLUCIDE®), ribavirin (Virazole), endonuclease inhibitors, matrix M1 inhibitors, antibodies to viral proteins, Vis-410, nitazoxanide, NT-300, fludase, alferon, PUR003, EV-077, surfaxin, and homspera. In one embodiment, the anti-viral agent is oseltamivir. Oseltamivir treatment for infected subjects is dosed at 75 mg twice a day for 5 days.

According to certain aspects, the antiviral agent may be a monoclonal antibody, such as an antibody against the spike protein of the infecting virus. For example, each of casirivimab and imdevimab, antibodies provided as a cocktail by Regeneron as REGEN-COV™ that bind to nonoverlapping epitopes of the spike protein RBD of SARS-CoV-2. Additional examples include bamlanivimab plus etesevimab, which are neutralizing monoclonal antibodies that bind to different but overlapping epitopes in the spike protein RBD of SARS-CoV-2; and sotrovimab, which is a monoclonal antibody that targets an epitope in the RBD of the spike protein that is conserved between SARS-CoV and SARS-CoV-2.

The antiviral agents, including the monoclonal antibodies, may be administered before any symptoms of the viral infection are noted, such as after a positive results of direct SARS-CoV-2 viral testing (PCR or rapid antigen test). For example, the antiviral agents may include 600 mg of casirivimab and 600 mg of imdevimab administered together as a single intravenous infusion, or as to four subcutaneous injections, as soon as possible after positive SARS-CoV-2 viral testing (e.g., at days −10, −9, −8, −7, −6, −5, −4, −3, −2, −1, 0, or 1 of the administration of the systemic and/or local miltefosine) and within 10 days of symptom onset. The antiviral agents may include a 500 mg intravenous infusion of sotrovimab administered as a single intravenous infusion as soon as possible after positive SARS-CoV-2 viral testing (e.g., at days −10, −9, −8, −7, −6, −5, −4, −3, −2, −1, 0, or 1 of the administration of the systemic and/or local miltefosine) and within 10 days of symptom onset.

For individuals in whom repeat dosing is determined to be appropriate for ongoing exposure to SARS-CoV-2 for longer than 4 weeks and who are not expected to mount an adequate immune response to complete SARS-CoV-2 vaccination, the initial dose is 600 mg of casirivimab and 600 mg of imdevimab by subcutaneous injection or intravenous infusion followed by subsequent repeat dosing of 300 mg of casirivimab and 300 mg of imdevimab by subcutaneous injection or intravenous infusion once every 4 weeks for the duration of ongoing exposure.

(c) Immunomodulatory Agents

According to certain aspects, the secondary agent is an immunomodulatory agent. Exemplary immunomodulatory agents include at least interferons, immunoglobulin, IL-1 agonists, IL-6 agonists, TNF blockers, ulinastatin, hydroxychloroquine, and chloroquine. Such agents may address cytokine storm in a subject in need thereof.

Early administration of interferons, such as during the first few days of the treatment methods disclosed herein, may have certain benefits in reducing viral load. For example, the interferon IFN-λ primarily activates epithelial cells and reduces the mononuclear macrophage-mediated proinflammatory activity of IFN-αβ, and additionally inhibits the recruitment of neutrophils to the sites of inflammation. SARS-CoV and MERS-CoV mainly infect alveolar epithelial cells (AEC), thus IFN-λ may activate the antiviral genes in epithelial cells, thereby exerting antiviral effects without overstimulating the human immune system.

Moreover, inhaled interferon beta-1a (IFN α-2b) and interferon beta-1a (IFN β-1a) are found to improve recovery of subjects hospitalized with Covid-19 (speed ambulation, decrease risk of developing sever disease, and reduce breathlessness. Subcutaneous interferon beta-1b (IFN β-1b) is found to provide clinical improvement as assessed by the National Early Warning Score (NEWS) 2 and Sequential Organ Failure Assessment (SOFA) score and a shorten hospital stay for subjects hospitalized with Covid-19.

Accordingly, exemplary interferons useful in the present invention include at least IFN α-2b, IFN β-1a, and IFN β-1b, which are cytokines in the interferon family. Exemplary doses of IFN β-1b include a dose of 0.0625 mg, 0.125 mg, 0.1875 mg, or 0.25 mg injected subcutaneously every other day. The dose may increase over time, such as starting at the 0.0625 mg dose and ending at the 0.25 mg dose over the course of 6 weeks, wherein the dosing may be continued at the 0.25 mg dose thereafter. Alternatively, IFN β-1b may be dosed at 8 million IU (250 ug) by subcutaneous injection every other day for up to 7 doses total (14 days). Administration of the interferon(s) may be initiated before the systemic formulation of miltefosine of with the systemic formulation of miltefosine (e.g., at days −10, −9, −8, −7, −6, −5, −4, −3, −2, −1, 0, or 1).

Another exemplary immunomodulatory agent includes vitamin D. Vitamin D is a group of fat-soluble secosteroids, including vitamins D3 and D2. Vitamin D is known to boost the immune system by regulating Th1 and Th2 cells to prevent autoimmune responses. Vitamin D is also involved in RAS and may help to reduce renin, both of which may act to reduce or stop the bradykinin storm observed with certain viral infections, such as Covid-19. RAS includes a cascade that leads to the generation of angiotensin II (Ang II), the main effector of the system. The rate-limiting component of the RAS is renin. This, administration of vitamin D may reduce renin, slow or stop RAS, and reduce the concentration of bradykinin in a subject.

Vitamin D may be administered orally, such as in strengths from 50 to 50,000 international units (IU), as a soft gel, capsule, tablet or liquid. Exemplary doses according to aspects of the presently disclosed invention include 100-5,000 IU per kilogram body weight taken by mouth daily for at least three days; or 10,000-100,000 IU taken by mouth weekly for at least 4 weeks; 1,000-50,000 IU taken by mouth D daily for at least 6 months; 10.0 and 100 μg per day for vitamin D, or 0.25 and 50 μg per day per hydroxy derivatives of vitamin D. A preferred dose of vitamin D compound for the present invention is the maximum that a subject can tolerate and not develop serious hypercalcemia.

The vitamin D may be vitamin D2 or D3, or analogs thereof (e.g., 1α,25-dihydroxyvitamin D3, 19-nor-1,25-dihydroxyvitamin D2, 24-homo-22-dehydro-22E-1α,25-dihydroxyvitamin D3, 1,25-dihydroxy-24(E)-dehydro-24-homovitamin D3, or 19-nor-1,25-dihydroxy-21-epi-vitamin D3).

(d) Steroidal Agents

According to certain aspects, the secondary agent may be a steroidal agent, such as a corticosteroid. Corticosteroids are a class of steroid hormones that have anti-inflammatory functions. Timely administration of corticosteroids, such as glucocorticoids, may reduce fever, relieve radiation infiltration of the lung (e.g., such as after radiotherapy treatment used as an anti-inflammatory and to reduce the burden of inflammatory cells infiltrating the lungs), and improve oxygenation. The timing of administration and the dosage of glucocorticoids has been found to be very important to the outcome of the severely ill subjects. A too early administration of glucocorticoids inhibits the initiation of the body's immune defense mechanism, thereby increasing the viral load and ultimately leading to adverse consequences.

Thus, according to aspects of the presently disclosed invention, steroid administration, such as glucocorticoids may be later in the therapy protocol and may be used in critically ill subjects suffering inflammatory cytokine storm. Inhibition of excessive inflammation through timely administration of glucocorticoids in the early stage of inflammatory cytokine storm effectively prevents the occurrence of acute respiratory disease and may protect the functions of the subjects' organs. For subjects with progressive deterioration of oxygenation indicators, rapid imaging progress, and excessive inflammatory response, the use of glucocorticoid in the short term (3-10 days) is appropriate, and the recommended dose is no more than equivalent to methylprednisolone 1-2 mg/kg/day. Dexamethasone, another exemplary corticosteroid, may be administered orally (tablet, solution) or via IV at doses of 6 mg once daily, for up to 10 days or until hospital discharge.

Accordingly, corticosteroids may be administered at an early stage of inflammatory cytokine storm. For example, according to methods of the present invention, a positive viral diagnosis may indicate immediate initiation of treatment with a corticosteroid (e.g., at days −10, −9, −8, −7, −6, −5, −4, −3, −2, −1, or 0 of the administration of the systemic and/or local miltefosine) and may include treatment with the corticosteroid for 1 to 10 days.

Alternatively, corticosteroids may be administered at an early stage of inflammatory cytokine storm, but not before certain indicators are present, e.g., not in the absence of inflammatory markers. For example, according to methods of the present invention, a positive viral diagnosis, or onset of certain viral symptoms (e.g., oxygen saturation level drops below normal, such as below 96%, or below 94%, or below 92%, or below 90%, or below 88%, or even below 86%), may indicate immediate initiation of treatment with Miltefosine (day 1), and may include treatment with a corticosteroid starting at day 1, 2, 3, 4, 5, 6, 7, 8, or later depending on the health status (e.g., inflammation) of the subject.

Certain other steroids that may directly address the bradykinin storm observed as the result of certain viral infections, e.g., Covid-19, include at least danazol (Danocrine®), supplied in 50, 100, and 200 mg oral capsule, dosed as 50 to 400 mg two or three times per day, for a total of 100 to 800 mg per day); stanozolol (Winstrol®, supplied as 2 mg tablets taken orally 2 to 3 times per day), and ecallantide (Kalbitor®, supplied as a subcutaneous injection of 10-30 mg). These FDA approved drugs may reduce bradykinin production and could potentially stop a deadly bradykinin storm. Others, like icatibant (Firazyr®), supplied as a subcutaneous injection of 30 mg), may reduce bradykinin signaling.

(e) Antipyretic Agents

According to certain aspects, the secondary agent is an antipyretic agent, such as ibuprofen, naproxen, ketoprofen, nimesulide, aspirin, and other non-steroidal anti-inflammatory drugs, and acetaminophen.

(f) Anti-Anaphylaxis Agents

According to certain aspects, the secondary agent is an anti-anaphylaxis agent such as epinephrine and diphenhydramine, or antioxidants such as selenium, glutamine, vitamin E, and eicosapentaenoic acid.

Thus, methods according to the presently disclosed invention, which include systemic and optional local administration of miltefosine, may also include administration of an immunomodulatory agent such as an interferon or vitamin D, or a steroid as a secondary agent, either orally or topically, for management of inflammation. Moreover, it is possible that treatment with steroids may reduce the autoimmune response, cytokine storm, such as may occur after miltefosine treatment has been successful in killing the virus. Treatment with vitamin D may address certain of the issues related to bradykinin storms observed after a viral infection, such as with covid-19.

Accordingly, methods of the presently disclosed invention may include administration of a steroidal agent after the first days of treatment with the systemic miltefosine, or after the loading dose of miltefosine (i.e., systemic or local steroids may be administered during a sustained or second dose period of the miltefosine). Specific steroids as well as formulations and administration routes (i.e., oral, intravenous, topical) may be those commonly known and used. An exemplary steroid includes the corticosteroid, glucocorticoid, administered during a second dose time period for 3-5 days.

Packs and Kits

The compositions of the presently disclosed invention may, if desired, be presented in a pack or dispenser device which may contain one or more unit dosage forms of the miltefosine. The pack may, for example, comprise metal or plastic foil, such as a blister pack. The dispenser device may, for example, comprise a bottle. The pack or dispenser device may be accompanied by instructions for administration, thus forming a kit.

According to certain aspects of the presently disclosed invention, the systemic formulation of miltefosine may be provided in a kit for carrying out the therapeutic methods of the invention. As such, the instructions may include directions for administration of an oral formulation of miltefosine, which may comprise directing the subject or caregiver to administer a unit dose of the oral formulation at least two times per day (BID) for at least one day, such as at least 2, 3, 4, 5, 6, 7, 8, 9, or 10 days, to provide a total first daily dose According to certain aspects, the instructions may further comprises administering the oral formulation of miltefosine at least two times per day (BID) for at least one day, such as at least 3 days to 3 months, to provide a total second daily dose. The second daily dose may be administered for a second time period extending beyond a first time period, i.e., subsequent to the first time period, such as the time period of administration of the total first daily dose.

According to certain aspects of the presently disclosed invention, the systemic formulation of miltefosine and one or more secondary agents may be provided in a kit for carrying out the therapeutic methods of the invention. As such, the instructions may include directions for administration of the systemic formulation of miltefosine, which may comprise directing the subject or caregiver to administer a unit dose of the systemic formulation at least two times per day (BID) during a first and optionally, during a second time period, and administration of the one or more secondary agents. As such, the miltefosine may be provided in the kit in unit doses, such as pills of 10 mg, 50 mg, 100 mg unit dosage, or any unit dose described herein.

According to certain aspects, the instructions may indicate a delay in administration of the secondary agent, such as a delay of at least 1 day, or 2, 3, 4, 5, 6, or 7 days after the start of the miltefosine administration. According to certain aspects, the instructions may indicate that the one or more secondary agents are administered during the first and/or second time period.

According to certain aspects, a secondary agent included in the kit may be an interferon, such as any of those detailed herein, and the instructions may direct the subject or caregiver to administer the interferon during the first time period at any of the doses detailed herein. According to a specific example, the secondary agent included in the kit may be IFN β-1b included as a solution or desiccated powder that may be reconstituted to form a solution, such that a dose of 0.0625 mg, 0.125 mg, 0.1875 mg, or 0.25 mg may injected subcutaneously every other day as disclosed hereinabove. For example, the kit may include a solution formulated to provide a unit dose of 8 million IU (250 ug) for subcutaneous injection every other day for up to 7 doses total (14 days).

According to certain aspects, the secondary agent may be a corticosteroid, and the instructions may direct the subject or caregiver to administer the corticosteroid during the second time period, such as for up top ten days during the second time period (e.g., such as from the start of the second time period), or after a delay of at least 1 day after the start of the first time period. The corticosteroid may be any of those detailed herein at doses detailed herein or known in the art. According to a specific example, the secondary agent included in the kit may be dexamethasone provided for oral administration (tablet, capsule, solution) or IV administration (solution) at doses of 6 mg once daily, for up to ten days or until hospital discharge.

According to certain aspects, the secondary agent may be vitamin D or a derivative thereof, such as vitamin D3 or a derivative thereof, and the instructions may direct the subject or caregiver to administer the vitamin D during all or a portion of the first time period, or during all of the first time period and all or a portion of the second time period. The vitamin D may be administered at any of the doses detailed herein or known in the art.

According to certain aspects of the presently disclosed invention, a systemic formulation of miltefosine and a local formulation of miltefosine may be provided in a kit for carrying out the therapeutic methods of the invention. As such, the instructions may include directions for administration of a systemic formulation of miltefosine, i.e., oral, and a local formulation of miltefosine, i.e., inhaled formulation, which may comprise directing the subject or caregiver to administer a unit dose of the systemic and local formulations at least two times per day (BID) for at least one week. The local formulation may be a formulation that is inhaled into the lungs, such as through an inhaler or nebulizer. According to certain aspects, the systemic formulation of miltefosine may be a capsule or tablet, and the local formulation of miltefosine may be provided as an inhaler prefilled with aerosolizable miltefosine granules or power.

According to certain aspects of the presently disclosed invention, the systemic formulation of miltefosine, the local formulation of miltefosine, and one or more secondary agents may be provided in a kit for carrying out the therapeutic methods of the invention. For example, when the secondary agent is a steroid or vitamin D, either or both may be provided in the kit as an oral formulation, e.g., tablet, capsule, or liquid, in addition to the systemic and/or local formulations of miltefosine.

Such kits may include one or more containers having the various therapeutically effective amounts of the miltefosine and the secondary agent(s) provided in pharmaceutically acceptable form. For example, the kits may comprise a solid dosage form of miltefosine for oral systemic administration provided in a bottle or blister pack, and solid or liquid forms of the one or more secondary agents. For example, when the secondary agent includes vitamin D, it may be included in the kit as an oral formulation, e.g., capsule. When the secondary agent includes an interferon, it may be a solution formulated for subcutaneous administration. When the secondary agent is a corticosteroid, it may be included in the kit as an oral or subcutaneous formulation. Agents formulated for subcutaneous or IV administration may be provided in a concentrated form in a vial. As such, the kit(s) may further include a pharmaceutically acceptable solution, e.g., in combination with sterile saline or a buffered solution, or other pharmaceutically acceptable sterile fluid useful for dilution. Alternatively, the agents formulated for subcutaneous or IV administration may be lyophilized or desiccated; in this instance, the kit optionally further comprises in a container a pharmaceutically acceptable solution (e.g., saline, etc.), preferably sterile, to reconstitute the complex to form the liquid composition.

What is claimed is:

1. A method for treating a viral infection in a subject, the method comprising:
    administering a systemic formulation of hexadecylphosphocholine (miltefosine) for at least two days at a total dose of 50 mg/day to 200 mg/day,
    wherein the systemic formulation of miltefosine is provided as an oral formulation that is administered two or three times per day in evenly divided doses for at least seven days.

2. The method of claim 1, wherein day one of administration of the systemic formulation of miltefosine is initiated when the subject's oxygen saturation level drops below 96%.

3. The method of claim 1, wherein day one of administration of the systemic formulation of miltefosine is initiated upon a positive diagnosis of the viral infection and after the subject's oxygen saturation level drops below 96%, but before the subject is placed on oxygen therapy.

4. The method of claim 1, wherein day one of administration of the systemic formulation of miltefosine is initiated upon a positive diagnosis of the viral infection and categorization of the subject as high risk, or as having a high viral load.

5. The method of claim 1, further comprising:
    administering an effective amount of a local formulation of miltefosine, wherein the local formulation of miltefosine comprises an aerosolizable formulation to be inhaled nasally or orally by the subject.

6. The method of claim 1, further comprising:
    administering an effective amount of one or more secondary agents, wherein the secondary agents comprise one or more PI3K/AKT/mTOR inhibitors, antiviral agents, immunomodulatory agents, steroids, antipyretic agents, and anti-anaphylaxis agents.

7. The method of claim 6, wherein the one or more secondary agents comprise an interferon, vitamin D, or a combination thereof.

8. The method of claim 6, wherein the one or more secondary agents comprise a corticosteroid administered for up to ten days beginning before initiation of the miltefosine administration, or on the same day as initiation of the miltefosine administration.

9. The method of claim 6, wherein the one or more secondary agents comprise a monoclonal antibody against a spike protein of the viral infection beginning before initiation of the miltefosine administration, or on the same day as initiation of the miltefosine administration.

10. The method of claim 6, wherein the viral infection is caused by an influenza virus or a coronavirus.

11. A method for treating a viral infection in a subject, the method comprising:
    administering an oral formulation of hexadecylphosphocholine (miltefosine) at a first dosage of about 50 mg/day to about 200 mg/day for a first time period of at least one day; and
    administering the oral formulation of miltefosine at a second dosage of about 10 mg/day to about 150 mg/day for a second time period extending beyond the first time period, wherein the second time period is from at least three days to one month,
    wherein day one of administration of the oral formulation is initiated when one or more of the following occur: (i) the subject's oxygen saturation level drops below 95%, (ii) the subject's viral load is above normal, and (iii) the subject is in a high-risk category.

12. The method of claim 11, further comprising:
    administering an effective amount of one or more secondary agents, wherein the secondary agents comprise one or more a PI3K/AKT/mTOR inhibitor, an antiviral agent, an immunomodulatory agent, a steroid, an antipyretic agent, and an anti-anaphylaxis agent.

13. The method of claim 12, wherein the one or more secondary agents comprise any one or more of (i) the immunomodulatory agent comprising an interferon, vitamin D, or a combination thereof; (ii) the steroid comprising a corticosteroid administered for up to ten days beginning before initiation of the miltefosine administration, or on the same day as initiation of the miltefosine administration; and (iii) the antiviral agent comprising a monoclonal antibody against a spike protein of the viral infection beginning before initiation of the miltefosine administration, or on the same day as initiation of the miltefosine administration.

14. The method of claim 11, wherein the viral infection is caused by an influenza virus or a coronavirus.

15. The method of claim 11, wherein the viral infection is caused by a severe acute respiratory syndrome coronavirus (SARS-CoV).

16. The method of claim 11, wherein the first dosage and the second dosage are each administered at least two times per day in evenly split doses.

17. A kit for the treatment of a viral infection caused by an influenza virus or a coronavirus, the kit comprising:
    an oral formulation of miltefosine comprising 10 mg to 100 mg per unit dose;
    one or more of a secondary agent selected from a steroid, an interferon, an anti-viral, or combination thereof; and instructions on an administration regime for the oral formulation of miltefosine and the one or more secondary agent, wherein the administration regime for the oral formulation of miltefosine comprises at least two unit doses per day for a combined first dose of about 50 mg/day to about 200 mg/day for a first time period of at least one day.

18. The kit of claim 17, wherein the administration regime for the oral formulation of miltefosine further comprises at least two unit doses per day for a combined second dose of about 10 mg/day to about 150 mg/day for a second time period extending beyond the first time period, wherein the second time period is from at least three days to one month.

19. The kit of claim 17, wherein the steroid is dexamethasone provided as a unit dose of 6 mg for oral or IV administration once daily for up to ten days, and wherein the interferon is IFN b-1b provided as a unit dose of 8 million units for subcutaneous administration every other day for up to seven days, and wherein the anti-viral is a monoclonal antibody against a spike protein of the viral infection.

\* \* \* \* \*